United States Patent
Mathisen et al.

(10) Patent No.: US 8,911,504 B2
(45) Date of Patent: Dec. 16, 2014

(54) ELASTICALLY DEFORMABLE AND RESORBABLE MEDICAL MESH IMPLANT

(75) Inventors: Torbjörn Mathisen, Älvsjö (SE); Henrik Magnusson, Uppsala (SE)

(73) Assignee: Novus Scientific AB, Uppsala (SE)

( * ) Notice: Subject to any disclaimer, the term of this patent is extended or adjusted under 35 U.S.C. 154(b) by 717 days.

(21) Appl. No.: 12/914,258

(22) Filed: Oct. 28, 2010

(65) Prior Publication Data
US 2012/0109165 A1 May 3, 2012

(51) Int. Cl.
*A61F 2/02* (2006.01)
*D04B 21/12* (2006.01)
*A61F 2/00* (2006.01)

(52) U.S. Cl.
CPC ......... *A61F 2/0063* (2013.01); *A61F 2250/003* (2013.01); *A61F 2250/0017* (2013.01); *D10B 2509/08* (2013.01); *A61F 2250/0028* (2013.01); *D04B 21/12* (2013.01); *A61F 2250/0029* (2013.01)
USPC .................................................. 623/23.72

(58) Field of Classification Search
None
See application file for complete search history.

(56) References Cited

U.S. PATENT DOCUMENTS

| | | | |
|---|---|---|---|
| 8,016,841 B2 | 9/2011 | Magnusson et al. | |
| 8,083,755 B2 | 12/2011 | Mathisen et al. | |
| 8,313,499 B2 | 11/2012 | Magnusson et al. | |
| 2006/0142786 A1 | 6/2006 | Mathisen et al. | |
| 2008/0306494 A1 | 12/2008 | Magnusson et al. | |
| 2009/0326565 A1 | 12/2009 | Trabucco et al. | |
| 2011/0112561 A1 | 5/2011 | Mathisen et al. | |
| 2012/0083807 A1 | 4/2012 | Mathisen et al. | |
| 2012/0184973 A1 | 7/2012 | Mathisen et al. | |
| 2013/0012968 A1 | 1/2013 | Magnusson et al. | |

FOREIGN PATENT DOCUMENTS

| | | |
|---|---|---|
| EP | 0 677 297 A1 | 10/1995 |
| EP | 1 212 986 A1 | 6/2002 |
| EP | 1 674 048 A1 | 6/2006 |
| EP | 2 002 800 B1 | 9/2009 |
| WO | WO 01/85061 A2 | 11/2001 |

OTHER PUBLICATIONS

Swedish Office Action dated Dec. 16, 2011, 4 pages.
European Search Report dated Feb. 2, 2012, 7 pages.

*Primary Examiner* — Darwin Erezo
*Assistant Examiner* — Son Dang
(74) *Attorney, Agent, or Firm* — Foley & Lardner LLP

(57) ABSTRACT

The invention relates to a polymeric mesh implant for use in reconstruction of tissue defects, which mesh implant comprises a first set of fibers arranged in a first knit pattern comprising apertures, wherein each aperture, or a subset thereof, comprises an elastic fiber arranged in a first direction of the mesh implant such that when the mesh implant is stretched in this first direction, the elastic fibers are elongated and also exert a restoring force on the first knit pattern.

2 Claims, 1 Drawing Sheet

ELASTICALLY DEFORMABLE AND RESORBABLE MEDICAL MESH IMPLANT

FIELD OF THE INVENTION

The present invention relates to a resorbable polymeric mesh implant used in the medical reconstruction of soft tissue defects, and particularly to an elastically deformable and resorbable polymeric mesh, and even more particularly to a resorbable polymeric mesh whose knit pattern comprises elastic fibers arranged such that an elastically deformable mesh implant is obtained.

BACKGROUND OF THE INVENTION

Resorbable polymeric mesh implants are known. European Patent No. 1 674 048, which is assigned to the present assignee, describes a resorbable polymeric mesh implant comprising at least two materials, wherein the second material is substantially degraded at a later point in time than the first material following the time of implantation. The mesh implant is adapted to have a predetermined modulus of elasticity that gradually decreases until the implant is completely degraded and subsequently absorbed.

European Patent No. 2 002 800, which is assigned to the present assignee, also describes a resorbable polymeric mesh implant comprising at least two materials having different degradation times. The first material, which has the shorter degradation time, is in the form of a first set of polymer fibers which are arranged in a first knit pattern, and the second material, which has the longer degradation time, is in the form of a second set of polymer fibers which are arranged in a second knit pattern, wherein the fibers of the first knit pattern lock movement of the second knit pattern by traversing apertures of the second knit pattern. When the first set of fibers has degraded, the second knit pattern can move more freely, which results in a more compliant mesh implant. A mesh fabricated according to the specifications of EP 1 674 048 and EP 2 0028 00 is by the present assignee marketed under the trademark TIGR®. This mesh can in its initial, undegraded state be characterized as inelastic, and is in its semi-degraded state, when the polymer fibers of the first set have degraded, be characterized as not reversible deformable. The entire contents of both of these European patents are incorporated herein by reference for the materials, compositions, devices, implants, processes and techniques relating to mesh implants discussed therein.

Although mesh products produced according to the specifications of the patents listed above fulfill their intended purpose very well, the mechanical characteristics of these meshes are for some medical applications not ideal. In particular, the meshes do not exhibit a true elastic behavior, i.e. they are not reversibly deformable.

SUMMARY OF THE INVENTION

A general object of the present invention is therefore to provide an elastic and resorbable medical mesh implant, which after deformation, i.e. stretching, resumes its original shape, or at least almost resumes its original shape.

According to the present invention, a medical mesh implant comprises a first set of fibers having a first degradation time. The fibers of the first set are arranged in a first knit pattern with, inter alia, a predetermined number of openings or apertures per area unit. In all, or optionally some, of these apertures, an elastic fiber is arranged such that when the mesh and thereby the first knit pattern is stretched in a first direction, the elastic fibers are subjected to a force (stress), which causes an elongation or length deformation (strain) of the elastic fibers. When the stretching of the mesh implant is discontinued and the mesh is released and free to relax, the elastic fibers resume their original lengths. The shape of the first knit pattern is thereby restored, and the whole mesh implant will consequently resume its original shape.

In embodiments of the present invention, a mesh is assumed to a have a first direction and a second direction. (In a woven or knitted mesh product, the first and second mesh directions may optionally coincide with the warp direction and weft direction, respectively, or coincide with other "natural" directions.) In a first embodiment, the elastic fibers are arranged in only one direction of the mesh; and in another embodiment the elastic fibers are arranged in two, preferably perpendicular, directions of the mesh. Other directional arrangements for the elastic fibers are also within the scope of the present invention.

In embodiments of the present invention, the elastic fibers are preferably made from a biodegradable and resorbable polymer having a degradation time that can be longer, shorter or comparable to the degradation time of the first set of fibers.

In further embodiments of a mesh implant according to the present invention, a mesh implant comprises elastic fibers which, as in the embodiments described above, are arranged in apertures formed in a first knit pattern of a first set of fibers. In these further embodiments, the fibers of the first set are however supplemented with a second set of fibers whose degradation time is shorter than the degradation time of the elastic fibers. The fibers of the second set can be arranged in a second knit pattern, such that the second knit pattern locks movement of the first knit pattern by traversing the apertures of the first knit pattern. The fibers of the second set can have a high modulus of elasticity such that the mesh initially can be characterized as inelastic. The elastic behaviour of a mesh implant according to these embodiments will thereby come into play once the fibers of the second set have been degraded.

The fibers of the first set and/or the fibers of the second set and/or the elastic fibers can be made from one or more of the materials described in the European Patents described above and/or other suitable materials.

DETAILED DESCRIPTION OF PREFERRED EMBODIMENTS

Figure 1A:
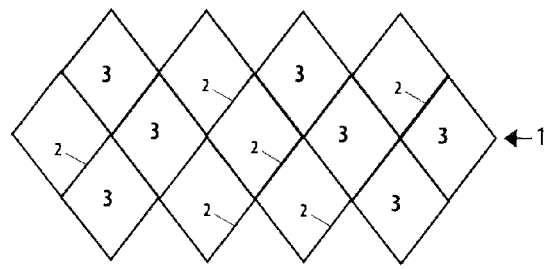
FIGS. 1a and 1b illustrate schematically the behavior of a prior art medical mesh implant, which is not the present invention.
Figure 1B:
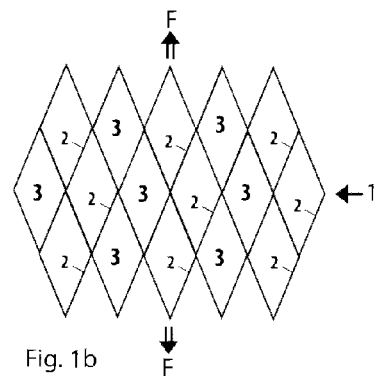

For a better understanding of the present invention, the mechanical behaviour of a conventional medical mesh implant 1, which is not the present invention, will first be outlined in conjunction with FIG. 1a and FIG. 1b. The mesh 1 comprises a number of individual fibers 2, which, in accordance with a specific knit pattern, have been knitted together to form a mesh 1, which, inter alia, comprises a predetermined number of apertures 3.

In FIG. 1a, the mesh 1 is shown in an initial or relaxed state, i.e. the mesh 1 is not subjected to any external forces. If a small or at least only moderately large force—denoted with F in FIG. 1b—is applied to the mesh 1, a deformation of the mesh 1 is introduced. More specifically, each of the apertures 3 of the mesh 1 undergoes a shape transformation from a more or less quadratic shape to an elongated rhombic shape, as is seen when comparing FIG. 1a with FIG. 1b. Here it should be appreciated that for small forces F this mesh deformation is basically to be attributed to the mesh structure itself, i.e. there is substantially no elongation of the individual fibers 2. The latter statement implies consequently that when the force F is removed, there are no significant forces that strive to bring the mesh 1 back to its original shape. Furthermore, since there is no elongation of the fibers 2, it is essentially insignificant whether the fibers 2 are made from an elastic material or an inelastic material. In other words, a conventional mesh implant like the mesh 1 does not exhibit an elastic behaviour when it is subjected to a force which only causes a deformation of the mesh structure, and such a mesh implant will not resume its original shape when this force is removed. To merely complete the picture, for large forces F the mesh 1 would be further deformed, and eventually also the individual fibers 2 would be stretched. When such a large force is removed, the mesh 1 would—if the fibers 2 are made from an elastic material—return to the deformed shape shown in FIG. 1b. The mesh would, however, not resume its original shape shown in FIG. 1a.

Figure 2A:
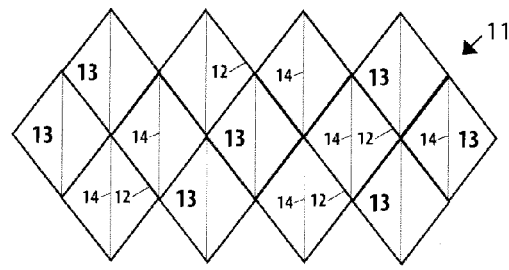
FIGS. 2a and 2b illustrate schematically a first embodiment of a medical mesh implant according to the present invention, with a knit pattern having apertures traversed by elastic fibers in one direction.
Figure 2B:
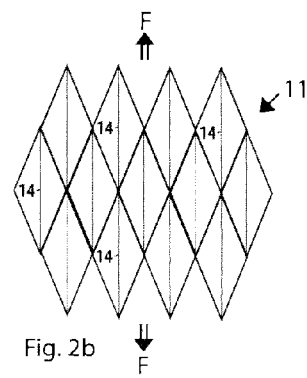

FIG. 2a and FIG. 2b illustrate a first embodiment of a mesh implant 11 according to the present invention. The mesh 11 comprises a first set of fibers 12, which are arranged in a first knit pattern such that a number of apertures 13 are formed in the mesh 11. The fibers 12 are preferably made from a resorbable polymer. Within an aperture 13, a fiber 14 is arranged, such that the fiber 14 traverses the aperture 13 and is connected to two points on the perimeter of the aperture 13. In this embodiment, each individual fiber 14 is connected to the corresponding points on the perimeter of an aperture 13 such that all of the fibers 14 extend in the same direction of the mesh implant 11, which direction may be denoted a first direction of the mesh implant 11. The fibers 14 are made from an elastic and preferably resorbable polymer. In FIG. 2a, the mesh 11 is shown in an initial or relaxed state, i.e. the mesh 11 is not subjected to any external forces. Following the same reasoning as in conjunction with the conventional mesh 1 above, if now a small or moderately large force—denoted F in FIG. 2b—is applied in the first direction of the mesh 11, a deformation of the mesh 11 is introduced. In contrast to the deformation of the conventional mesh 1 shown in FIGS. 1a and 1b, the deformation of the present mesh 11 involves not only distortion of the mesh structure but also an elongation of the elastic fibers 14. Therefore, when the force F is removed, the elongated elastic fibers 14 will according to Hook's law strive to resume their original lengths. When the elastic fibers 14 have resumed their original lengths, the whole mesh 11 has resumed its original shape, as shown in FIG. 2a. In other words, when the mesh 11 comprises elastic fibers 14 arranged in a suitable way in apertures 13 created by a first set of fibers 12 connected according to a first knit pattern, the mesh 11 exhibits an elastic behaviour, and an elastically deformable mesh implant 11 is produced.

In the embodiment shown in FIGS. 2a and 2b, each of the apertures 13 in the mesh 11 has been provided with a separate elastic fiber 14. In an alternative arrangement (not shown in the figures), only a subset (for example, one-half or one-quarter) of the apertures in a mesh implant could be provided with an elastic fiber.

Figure 3:
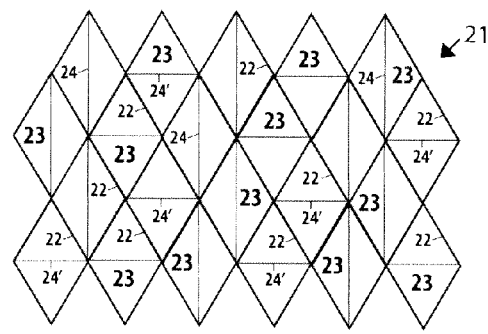
FIG. 3 illustrates schematically a second embodiment of a medical mesh implant according to the present invention, with a knit pattern having apertures traversed by elastic fibers in either of two directions.

As described above, the mesh 11 comprises elastic fibers 14, which are arranged in only one direction of the mesh 11. Other arrangements are also possible, and FIG. 3 illustrates a second embodiment of a mesh implant 21 according to the present invention. The mesh 21 comprises a first set of fibers 22, which are arranged in a first knit pattern such that a number of apertures 23 are formed in the mesh 21. The fibers 22 are preferably made from a resorbable polymer. Within a first subset of the apertures 23, an elastic fiber 24 is arranged such that the fiber 24 traverses the aperture 23 in a first direction and is connected to two points on the perimeter of the aperture 23, and within a second subset of the apertures 23, an elastic fiber 24' is arranged such that the fiber 24' traverses the aperture 23 in a second direction and is connected to two points on the perimeter of the aperture 23.

In the embodiment shown in FIG. 3, the first direction coincides with the vertical direction of the mesh (as depicted in the figure) and the second direction coincides with the horizontal direction of the mesh (as depicted in the figure). Other directional arrangements are also possible. For example, a third subset of the apertures in a mesh implant could be provided with an elastic fiber that traverses the aperture in a third direction, which is different from both the first direction and the second direction. Any other directional arrangements for the elastic fibers of a mesh implant are also within the scope of the present invention; and it is further possible that some of the apertures lack an elastic fiber. In particular, it may be preferable to let the direction (or directions) of the elastic fibers coincide with the expected direction (or directions) of the load which a mesh implant is designed to be subjected to. It may further be preferred to align the elastic fibers with other "given" directions in a mesh structure, such as the warp direction or weft direction of a woven mesh or corresponding directions in a warp knitted mesh; or the elastic fibers could be arranged more or less perpendicular to such given directions in a mesh structure.

From the above description it should be clear that with elastic fibers arranged in more than one direction of a mesh implant according to the present invention, the mesh will exhibit an elastic behaviour in more than one direction, i.e. the mesh implant will strive to resume its original shape as long as the components of a stretching force are directed along the directions of sufficiently many of the elastic fibers.

Figure 4:
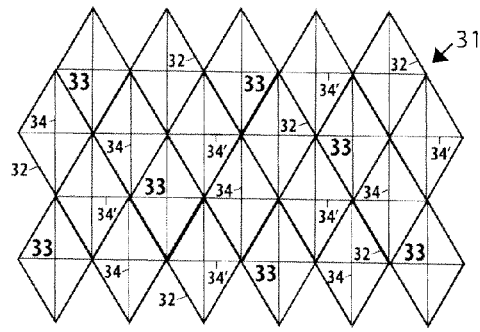
FIG. 4 shows schematically a third embodiment of a medical mesh implant according to the present invention, with a knit pattern having apertures traversed by elastic fibers in two directions.

In the embodiments described above in conjunction with FIGS. 2a-b and FIG. 3, respectively, an aperture contains at most one elastic fiber. It is however possible that an individual aperture in a mesh contains more than one elastic fiber, e.g. two fibers arranged two different directions. FIG. 4 illustrates a third embodiment of a mesh implant 31 according to the present invention. The mesh 31 comprises a first set of fibers 32, which are arranged in a first knit pattern such that a number of apertures 33 are formed in the mesh 31. The fibers 32 are preferably made from a resorbable polymer. Within an aperture 33, a first elastic fiber 34 is arranged such that the fiber 34 traverses the aperture 33 in a first direction and is connected to two points on the perimeter of the aperture 33. Within the same aperture 33, a second elastic fiber 34' is arranged such that the fiber 34' traverses the aperture 33 in a second direction and is connected to two points on the perimeter of the aperture 33. In this embodiment, the first direction and the second direction are perpendicular to each other, but other directional arrangements are within the scope of the present invention. For example, within an aperture, a third elastic fiber can be arranged such that the third elastic fiber traverses the aperture in a third direction, which is different from both the first direction and the second direction.

It should be appreciated that although an elastic fiber arranged in a one aperture and an elastic fiber arranged in another aperture have been described as two different elastic fibers, these two elastic fibers could in fact be the same physical fiber; i.e. it is the mesh forming technique (e.g. knitting or weaving) that creates two virtually different fibers. The same applies when there is more than one elastic fiber arranged within one aperture. Further, the term "connected" has herein been used to describe that an elastic fiber extends across an aperture and is connected to two points on the perimeter of the aperture. In a mesh, the apertures as well as the fiber arrangements are created by specific knit patterns, and there are numerous knit patterns that could be utilized to produce a mesh according to the present invention. Thus, the term "connected to" could have any meaning ranging from "being in contact with" to "attached to" or "knitted to".

Figure 5:
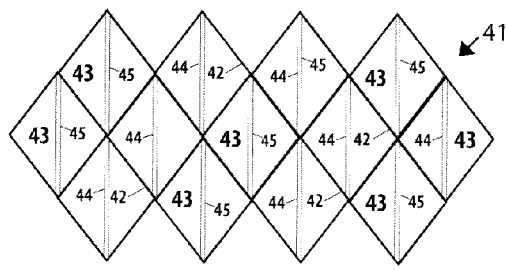
FIG. 5 shows schematically a fourth embodiment of a medical mesh implant according to the present invention, comprising a first set of fibers arranged in a first knit pattern and a second set of fibers arranged in a second knit pattern as well as elastic fibers, wherein apertures of the first knit pattern are traversed by both the fibers of the second set as well as the elastic fibers in the same direction.

FIG. 5 illustrates a fourth embodiment of a mesh implant 41 according to the present invention. The mesh 41 comprises a first set of fibers 42, which are arranged in a first knit pattern such that a number of apertures 43 are formed in the mesh 41. The fibers 42 are preferably made from a resorbable polymer. Within an aperture 43, a fiber 44 is arranged, such that the fiber 44 traverses the aperture 43 and is connected to two points on the perimeter of the aperture 43. The fibers 44 are made from an elastic and preferably resorbable polymer. In contrast to embodiments described above, the mesh implant 41 comprises further a second set of fibers 45, which are arranged in a second knit pattern. The second knit pattern can be designed such that the fibers 45 of the second set traverse apertures 43 created in the first knit pattern. The fibers 45 are preferably made from a resorbable polymer and have preferably a high modulus of elasticity. By suitable choice of first and second knit patterns, the fibers 45 of the second knit pattern will thereby lock movement of the first knit pattern in a first direction of the mesh implant 41. In the embodiment shown in FIG. 5, the fibers 45 are arranged along the elastic fibers 44. By choosing fibers 42, 44 and 45 such that the first fibers 42 have the longest degradation time, the high-modulus fibers 45 have the shortest degradation time, and the elastic fibers 44 have a degradation time which is between the degradation time of the high-modulus fibers 45 and the degradation time of the first fibers 42, a mesh implant 41 is achieved which initially can be characterized as inelastic, and which, when the second set of fibers 45 has degraded, can be characterized as elastically deformable. Instead of providing the high-modulus fibers 45 alongside the elastic fibers 44, the fibers 44 and fibers 45 could be interlaced with each other or spun together, such that the mesh implant 41 is produced (e.g. woven or knitted) with effectively only two different fibers, i.e. the slow resorbing fibers 42 and the combined fiber composed of fiber 44 and fiber 45.

In the embodiment described in conjunction with FIG. 5, the elastic fibers 44 and the high-modulus or inelastic fibers 45 extend in only one direction of the mesh implant 41. It is however possible to provide a mesh implant wherein elastic fibers and inelastic fibers, alongside each other, traverse apertures provided in a first knit pattern in more than one direction. Such a mesh would then have the same time-dependent mechanical behaviour as the mesh implant 41 but in more than one direction of the mesh implant.

Figure 6:
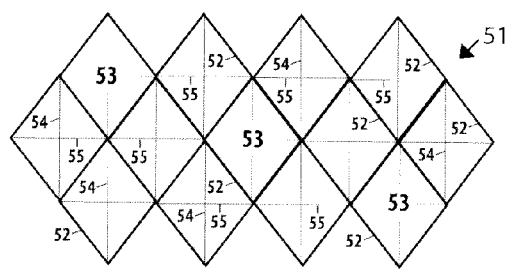
FIG. 6 shows schematically a fifth embodiment of a medical mesh implant according to the present invention, comprising a first set of fibers arranged in a first knit pattern and a second set of fibers arranged in a second knit pattern as well as elastic fibers, wherein apertures of the first knit pattern are traversed by the elastic fibers in a first direction and by the fibers of the second set in a second direction.

A perhaps more imaginative embodiment of a mesh implant according to the present invention is illustrated in FIG. 6. Here, a mesh implant 51 according to a fifth embodiment comprises a first set of fibers 52, which are arranged in a first knit pattern such that a number of apertures 53 are formed in the mesh 51. The fibers 52 are preferably made from a resorbable polymer. Within an aperture 53, a fiber 54 is arranged such that the fiber 54 traverses the aperture 53 in a first direction and is connected to two points on the perimeter of the aperture 53. The fibers 54 are made from an elastic and preferably resorbable polymer. The mesh implant 51 comprises further a second set of fibers 55, which are arranged in a second knit pattern. The second knit pattern is designed such that the fibers 55 of the second set traverse the apertures 53 in a second direction of the mesh implant 51. The fibers 55 are preferably made from a resorbable polymer and have preferably a high modulus of elasticity. By suitable choice of first and second knit patterns, the fibers 55 of the second knit pattern will thereby lock movement of the first knit pattern in the second direction of the mesh implant 51. Here it should however be noted that first and second directions are different from each other. By choosing fibers 52, 54 and 55 such that the first fibers 52 have the longest degradation time, the high-modulus fibers 55 have the shortest degradation time, and the elastic fibers 54 have a degradation time which is between the degradation time of the high-modulus fibers 55 and the degradation time of the first fibers 52, a mesh implant 51 is achieved which initially can be characterized as elastic in a first direction and inelastic in a second direction of the mesh implant 51, and which, at a later point in time when the second set of fibers 55 has degraded while the elastic fibers 54 and the first set of fibers 52 have not degraded, can be characterized as being elastically deformable in the first direction and being non-elastically deformable in the second direction.

The elastic fibers used in a mesh according to some embodiments of the present invention are preferably made from synthetic aliphatic polyesters, carbonates, or mixtures thereof. Non-limiting examples of such materials are those made through ring-opening polymerization of monomers such as lactide, glycolide, $\epsilon$-caprolactone, trimethylene carbonate, 1,5-dioxane-2-one (para-dioxanone), or 1,5-dioxepane-2-one. To achieve certain elastic properties in such material a prerequisite is that a certain amount of crystalline phase is present in said material to facilitate the fiber spinning process.

Preferably the elastic fiber is made from a block copolymer comprising a soft core, i.e. a glass transition temperature (Tg) below 30° C., and arms that have a certain amount of crystalline phase to facilitate the fiber spinning process. Typical examples of arm materials are those composed of more than 70 mole-% of L,L- or D,D-lactide, glycolide, 1,5-dioxane-2-one and $\epsilon$-caprolactone, while typical examples of materials for the soft core can be made from any of the above listed monomers to achieve a soft core having a Tg of 30° C., or less.

The block copolymer making up the elastic fiber can be comprised of a linear block copolymer having two arms or a so-called star polymer with three or more arms. The later copolymer can be initiated from a symmetrical or non-symmetrical initiator.

Yet other examples of synthetic resorbable polymers that can be used in part or in whole to form the elastic fiber are various aliphatic polyurethanes, such as polyureaurethanes, polyesterurethanes and polycarbonateurethanes, and also materials such as polyphosphazenes, polyorthoesters, or various copolymers of β-butyrolactones.

Poly-γ-butyrolactone and its various forms as produced in various bacterias, naturally occurring or manipulated, is easily transformed into an elastic fiber that can be used in the present invention as the elastic fiber, or in combination with any of the aforementioned materials, to form an elastic fiber fulfilling the intended purpose.

The first set of fibers according to the present invention is preferably made from synthetic aliphatic polyesters, carbonates, or mixtures thereof. Non-limiting examples of such materials are those made through ring-opening polymerization of monomers such as lactide, glycolide, ε-caprolactone, or 1,5-dioxane-2-one (para-dioxanone). To control the amount of crystalline phase in the material certain amount of trimethylene carbonate or 1,5-dioxepane-2-one can be copolymerized with any of the aforementioned monomers to achieve the material used in the first set of fibers.

Yet other examples of synthetic resorbable polymers that can be used in part or in whole to form the first set of fibers are various aliphatic polyurethanes, such as polyureaurethanes, polyesterurethanes and polycarbonateurethanes, and also materials such as polyphosphazenes, polyorthoesters, or various copolymers of (3-butyrolactones.

The elastic fibers used in the present invention can therefore be made from a plurality of various materials or combinations thereof such as blends to achieve the intended mechanical and degradable characteristic of the mesh. The fiber itself can be a homogeneous material or a bi- or tri-component fiber made from two or three different materials having various cross-sections such as side-by-side, sheath-and-core, island-in-the sea, or segmented structures.

Although the present invention has been described with reference to specific embodiments, also shown in the appended drawings, it will be apparent to those skilled in the art that many variations and modifications can be done within the scope of the invention as described in the specification and defined with reference to the claims below. It should in particular be noted that terms such as "elastically deformable" should not be interpreted too literally, which means that also a mesh implant provided in accordance with the present invention could exhibit some degree of hysteresis, i.e. the mesh will not necessarily resume exactly its original shape after having been subjected to an external, stretching force. The most important feature of the present invention is that by incorporating elastic fibers in a mesh, a restoring force is introduced which strives to bring the mesh implant back to its original shape after having been subjected to a stretching force. For example, according to some embodiments of the invention, if a mesh material (10 cm×10 cm) is fixed into a ball burst fixture as described in ASTM D3787 and deformed with a force corresponding to 16 Newton per centimeter for no longer than 15 seconds, the mesh will return to a shape where the residual deformation measured as the depth from the ball in its original position before the mesh was deformed and to the mesh surface one minute after load has been removed is less than 25%, or less than 15%, or less than 10%, or less than 5%. The original position of the ball is defined as a position where the ball is touching the surface of the mesh with a pre-load of 0.1 Newton. Also, although the various patterns of fibers described above may be formed by knitting or weaving, other techniques may be used to form the patterns.

What is claimed is:

1. A polymeric mesh implant for use in reconstruction of tissue defects, which mesh implant comprises:
   a first set of fibers arranged in a first knit pattern comprising apertures;
   an elastic fiber arranged in a first direction in at least a subset of apertures of the mesh implant such that when the mesh implant is stretched in this first direction, the elastic fibers are elongated and also exert a restoring force on the first knit pattern, the elastic fibers being arranged in a different knit pattern than the first knit pattern of the first set of fibers;
   a second set of fibers having a high modulus of elasticity and being arranged in a second knit pattern such that the fibers of the second set traverse apertures in the first knit pattern, and wherein the second knit pattern is arranged such that the fibers of the second set lock movement of the first knit pattern in the first direction of the mesh implant,
   wherein the fibers of the first set have a first degradation time, the elastic fibers have a second degradation time and the high-modulus fibers have a third degradation time, the first degradation time being the longest time and the third degradation time being the shortest and the second degradation time being therebetween.

2. A polymeric mesh implant for use in reconstruction of tissue defects, which mesh implant comprises:
   a first set of fibers arranged in a first knit pattern comprising apertures;
   an elastic fiber arranged in a first direction in at least a subset of apertures of the mesh implant such that when the mesh implant is stretched in this first direction, the elastic fibers are elongated and also exert a restoring force on the first knit pattern, the elastic fibers being arranged in a different knit pattern than the first knit pattern of the first set of fibers;
   a second set of fibers having a high modulus of elasticity and being arranged in a second knit pattern such that the fibers of the second set traverse apertures in the first knit pattern, and wherein the second knit pattern is arranged such that the fibers of the second set lock movement of the first knit pattern in a second direction of the mesh implant, the second direction being different from the first direction,
   wherein the fibers of the first set have a first degradation time, the elastic fibers have a second degradation time and the high-modulus fibers have a third degradation time, the first degradation time being the longest time and the third degradation time being the shortest and the second degradation time being therebetween.

* * * * *